United States Patent [19]

Cahalan et al.

[11] Patent Number: 5,767,108
[45] Date of Patent: Jun. 16, 1998

[54] METHOD FOR MAKING IMPROVED HEPARINIZED BIOMATERIALS

[75] Inventors: Patrick Cahalan, Geleen; Theo Lindhout, Gronsveld; Benedict Fouache; Michel Verhoeven, both of Maastricht; Linda Cahalan, Geleen; Marc Hendriks, Hoensbroek; Ron Blezer, Maastricht, all of Netherlands

[73] Assignee: Medtronic, Inc., Minneapolis, Minn.

[21] Appl. No.: 518,147

[22] Filed: Aug. 22, 1995

[51] Int. Cl.$^6$ ............................................. A61K 31/70
[52] U.S. Cl. .............................. 514/56; 514/2; 514/8; 514/802; 514/822; 530/393; 530/395; 536/21
[58] Field of Search ............... 536/55.1, 21; 514/56, 514/202, 222, 8, 825, 822; 530/363, 362, 391.9, 395, 922, 409, 710; 424/423; 436/529

[56] References Cited

U.S. PATENT DOCUMENTS

| | | | |
|---|---|---|---|
| 3,639,141 | 2/1972 | Dyck | 429/183 |
| 3,826,678 | 7/1974 | Hoffman et al. | 429/183 |
| 4,118,485 | 10/1978 | Eriksson et al. | 514/56 |
| 4,521,564 | 6/1985 | Solomon et al. | 525/59.1 |
| 4,526,714 | 7/1985 | Feijen et al. | 530/363 |
| 4,565,740 | 1/1986 | Golander et al. | 428/409 |
| 4,600,652 | 7/1986 | Solomon et al. | 424/423 |
| 4,613,665 | 9/1986 | Larm | 536/20 |
| 4,634,762 | 1/1987 | Feijen et al. | 530/350 |
| 4,642,242 | 2/1987 | Solomon et al. | 427/2.12 |
| 4,673,584 | 6/1987 | Nygren et al. | 427/2.1 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,049,403 | 9/1991 | Larm et al. | 427/2.1 |
| 5,053,048 | 10/1991 | Pinchuk | 623/1 |
| 5,055,316 | 10/1991 | Hoffman et al. | 530/359 |
| 5,077,372 | 12/1991 | Hu et al. | 602/48 |
| 5,132,108 | 7/1992 | Narayanan et al. | 429/78.17 |
| 5,229,172 | 7/1993 | Cahalan et al. | 427/536 |
| 5,292,724 | 3/1994 | Kita | 574/21 |
| 5,308,641 | 5/1994 | Cahalan et al. | 427/2.1 |
| 5,319,072 | 6/1994 | Uemura et al. | 530/393 |
| 5,350,800 | 9/1994 | Verhoeven et al. | 525/54.2 |
| 5,356,433 | 10/1994 | Rowland et al. | 623/11 |
| 5,415,938 | 5/1995 | Cahalan et al. | 428/409 |

FOREIGN PATENT DOCUMENTS

| | | |
|---|---|---|
| 0282091 | 9/1988 | European Pat. Off. |
| 1319007 | 5/1973 | United Kingdom |
| 2023022 | 12/1979 | United Kingdom |
| 9410938 | 5/1994 | WIPO |

*Primary Examiner*—Elli Peselev
*Attorney, Agent, or Firm*—Daniel W. Latham; Harold R. Patton

[57] ABSTRACT

A method of treating a patient with a medical device having immobilized heparin on a blood-contacting surface in which the covalently attached heparinized surface is provided with an adsorbed protein which may be activated by the immobilized heparin to block the coagulation of fibrinogen. Antithrombin III is the preferred adsorbed protein. The adsorbed protein is maintained on the immobilized heparin surface until the medical device is placed into contact with the patient's blood. When in contact with the patient's blood, the adsorbed protein will prevent initial thrombin formation at the biomaterial-blood interface. The preadsorption of ATIII is accomplished under conditions advantageous to maximum heparin/ATIII binding. When the preadsorbed surface comes in contact with whole blood, the maximum advantage of prophlactic properties of ATIII/heparin are obtained.

5 Claims, 1 Drawing Sheet

METHOD FOR MAKING IMPROVED HEPARINIZED BIOMATERIALS

BACKGROUND OF THE INVENTION

This invention relates to the enhancement of the biocompatibility of various surfaces having biomolecules which contain polysaccharide groups bound to the surface thereof and particularly to providing improved hemocompatability for biomaterials having heparin covalently attached thereto.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device. A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body.

As used herein, the solid surface of a biomaterial is characterized as "biocompatible" if it is capable of functioning or existing in contact with biological fluid and/or tissue of a living organism with a net beneficial effect on the living organism. One approach to improved biocompatibility for biomaterials is to attach various "biomolecules" such as growth factors, antimicrobial agents, antithrombogenic agents, and cell attachment proteins to the surface of the material.

Of particular concern for materials having surfaces in contact with blood is that the body's hemostatic process tends to be triggered by the presence of the material surface. The hemostatic process is normally initiated as the body's response to injury. When a vessel wall is injured, platelets adhere to damaged endothelium or exposed subendothelium. Following adhesion of the platelets, these cells cohere to each other preparatory to aggregation and secretion of their intracellular contents. Simultaneously there is activation, probably by electrostatic charge of the contact factors, of the coagulation cascade. The sequential step-wise interaction of these procoagulant proteins results in the transformation of soluble glycoproteins into insoluble polymers, which after transamidation results in the irreversible solid thrombus.

Immobilization of polysaccharides such as heparin to biomaterials has been researched extensively to improve bio- and hemocompatibility. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, covalent immobilization of heparin to a biomaterial consists of activating the material in such a way that coupling between the biomaterial and functional groups on the heparin (—COOH, —OH, —NH$_2$) can be achieved. For example, Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generation of thrombi and microemboli.

Besides the coupling of heparin via its natural functional groups or through a terminal aldehyde group, coupling of heparin via aldehyde groups randomly introduced into the chain by means of periodate oxidation has also been described. Solomon et al (in U.S. Pat. Nos. 4,600,652 and 4,642,242) and Hu et al (in U.S. Pat. Nos. 4,720,512; 4,786,556; 5,032,666 and 5,077,372) coupled heparin after periodate oxidation to an aminated polyurethane obtaining a material with high loading of stably bound heparin with the inventors claiming excellent antithrombogenicity for the material.

On surfaces where heparin is tightly attached by covalent bonds to a biomaterial surface with any unbonded or loosely bonded heparin removed by subsequent rinsing or other treatments of the surface, it has been observed that the surface can exhibit initial thrombogenicity even with high levels of active heparin on the surface. The reason for this is thought to be because the heparin is tightly bound to the material surface and is not released into the bulk of the blood and because biomaterial surfaces attract plasma proteins, including thrombin, which are capable of blocking the uptake of AT-III to the heparin on the surface. Thus, the formation of the AT-III complex with the bound heparin may be inhibited so that thrombin remains active.

It is therefore an object of the present invention to provide a biocompatible surface having active, covalently bonded heparin thereon which has improved AT-III activation upon contact with blood.

SUMMARY OF THE INVENTION

This and other objects are achieved by the present invention. We have discovered a method of treatment with a medical device having immobilized heparin on a blood-contacting surface in which the heparinized surface is provided with an adsorbed protein which may be activated by the immobilized heparin to block the coagulation of fibrinogen by thrombin. This invention is particularly useful for those surfaces which include heparin immobilized by covalent attachment to the surface since that heparin will not spontaneously separate itself from the surface. Several plasma proteins are known to inhibit the activity of thrombin and other serine proteases. AT-III is the preferred adsorbed protein in the present invention since it may be activated by heparin to inhibit thrombin and also because it inhibits other serine proteases of the coagulation pathways such as XIa, IXa, Xa, and XII.

The adsorbed protein is maintained on the immobilized heparin surface until the medical device is placed into contact with the patient's blood. When contacted with the patient's blood, the adsorbed ATIII will prevent initial thrombin formation at the biomaterial-blood interface, reducing platelet activation which would induce extra thrombin formation. As a consequence, build-up of thrombin at the bloodmaterial interface is prevented and the formation of a clot delayed. The preadsorption of ATIII is accomplished under conditions advantageous to maximum heparin/ATIII binding, and is not dimished by obvious competitive adsorption with other proteins in the whole blood to the heparin surface. When the preadsorbed surface comes in contact with the whole blood, the maximum advantage of prophylactic properties of ATIII/heparin can be obtained.

DETAILED DESCRIPTION OF THE INVENTION

Figure 1:
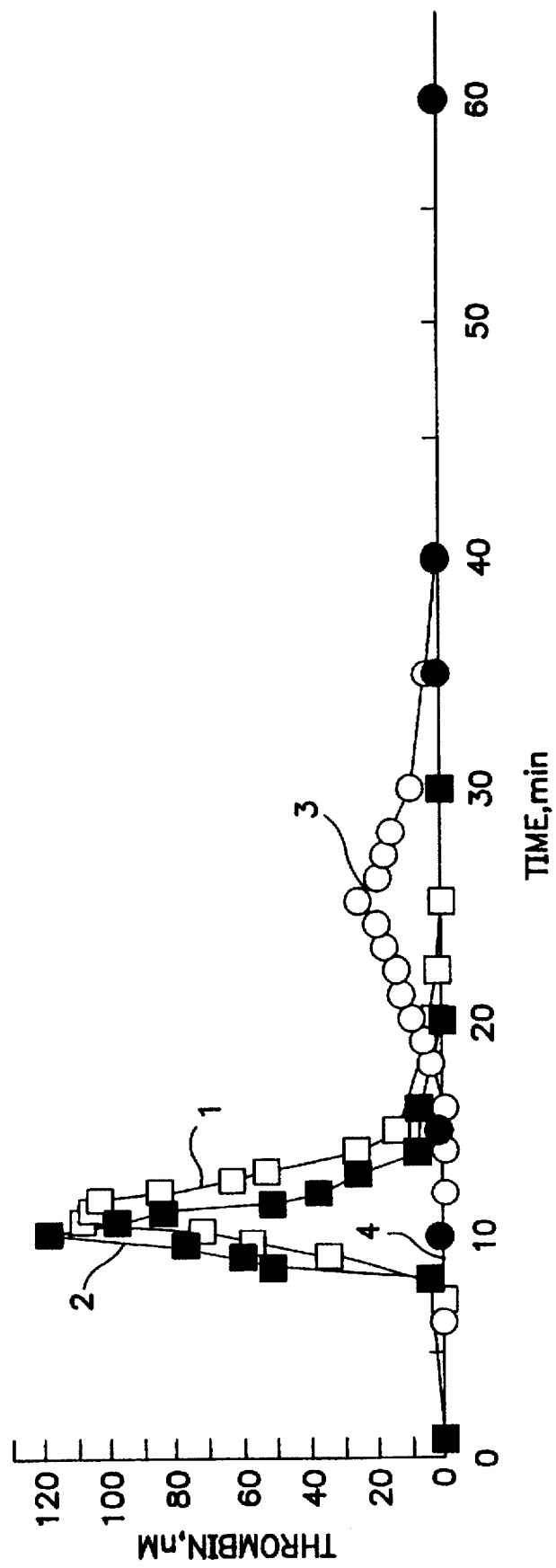
FIG. 1 is a plot of the thrombin generated by biomaterial surfaces as a function of time which provides a comparison of surfaces made according to the invention with other biomaterial surfaces.

In the present method, a medical device can be provided with a bloodcompatible surface of improved biocompatibility. By medical device, is meant devices which have surfaces which contact blood in the course of their operation, which blood is subsequently used in the circulatory system of patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves and the like which are implanted in blood vessels or in the heart. This can also include devices for temporary intravascular use such as catheters, guide wires and the like which are placed into the blood vessels or the heart for purposes of monitoring or repair.

An antithrombotic surface is provided by the immobilization of heparin to the surface of the device by covalent bonding. By heparin, we mean glycosaminoglycans, a heterogenous group of straight-chain anionic mucopolysaccharides, having anticoagulant properties. The heparin used herein can be a preparation obtained from tissues in a manner conventional for the preparation of heparin as an anticoagulant. The heparin preparation can be obtained from a variety of mammalian tissues, including, if desired, human tissue. Generally, porcine or bovine sources are used with a preferred tissue for heparin starting material being porcine intestinal mucosa. Heparin preparations prepared from this tissue source are commercially available.

Although many methods may be used for attaching the heparin, a preferred method is to provide the blood-contacting surface of the device with immobilized amine groups which are capable of bonding to aldehyde groups on the heparin molecule. Such amine groups can be provided by methods known to those skilled in the art. For example, amine-functional spacer molecules have been used to immobilize a biomolecule and/or biomolecules. The spacer insures that the active site of the biomolecule is held outward away from the support so as to contact the body fluid efficiently. The spacers are derived from organic molecules having at least two reactive functional groups, or more, generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radiofrequency plasma treatment by subjecting it to a radiofrequency electric field in the presence of a water vapor plasma medium. An aqueous solution of polyethyleneimine (PEI) and 1-(3dimethylpropyl)-3-carbodiimide (EDC) coupling agent was applied to the radiofrequency plasma discharge modified polyurethane surface. An aqueous solution of heparin and EDC was then applied to the PEI-treated surface in order to provide a polymeric surface having an anti-thrombogenic agent secured to its surface. However, considering the heterogeneity of the polyurethane surface even coating with the multi-functional spacer molecule is not guaranteed. Additional coverage can be provided, for example, according to U.S. Pat. No. 4,565,740 to Golander et al. or U.S. Pat. No. 5,049,403 to Larm et al. In the first of these patents, a complex of a polymeric cationic surfactant (e.g. a polyalkyleneimine) and a dialdehyde (e.g. glutaraldehyde) is adsorbed onto a substrate material. In the second of these patents, a polyamine is adsorbed onto the surface of a substrate and crosslinked with crotonaldehyde. Multiple coatings, including intermediate layers of anionic material are then applied to obtain an effective coating. However, these crosslinked coatings rely on adsorption onto the surface and ionic bonding to the surface, which may not provide good bonding of the coating to the surface. The inventors of the present invention have contributed to improvements in biocompatibility of biomaterials through the use of multilayer coatings in their U.S. Pat. Nos. 5,229, 172; 5,308,641 and 5,350,800 which are incorporated herein by reference. For example, in U.S. Pat. No. 5,229,172, we discovered a method for modifying the surface characteristics of a polymeric material by providing a base layer of grafted acrylamide on the polymeric surface which can be used to attach various spacers and biomolecules. Or, in U.S. Pat. No. 5,308,641, we discovered an improved spacer material which includes a polyalkyleneimine covalently attached to an aminated substrate and crosslinked with a crosslinking agent which is difunctional in aldehyde groups. Or, in U.S. Pat. No. 5,350,800, we discovered a method for attaching a biomolecule having carboxyl groups to an aminated solid surface by a carbodiimide and then selectively restoring the bio-functionality of the carboxyl groups.

On metal or glass surfaces, the binding of the base layer of such multi-layer coatings can be a problem since there is no organic structure to provide covalent bonds between the metal or glass substrate and the grafted base layer. Others have addressed the problem of binding to metals and glass by applying aminosilanes to adhere to the surface and then attaching the biomolecule to the aminosilane through the amine functionality of the aminosilane. This can be seen in U.S. Pat. No. 5,355,433 issued to Rowland et al in which an aminosilane is used to adhere a heparin molecule to an oxidized tantalum surface. Aminosilanes are also disclosed for attachment of a heparin molecule to glass or metal surfaces in U.S. Pat. No. 4,118,485 issued to Eriksson et al.

Preferably, the immobilized amine functionality is provided in a manner similar to that disclosed in our U.S. Pat. No. 5,308,641 in which a lightly crosslinked polyalkyeneimine is covalently attached to a substrate. By polyalkyleneimine, we mean to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkyleneimines employed in the present invention are preferably highly branched, thereby possessing primary, secondary, and tertiary amine groups. Thus, ethyleneimine polymerized by classical cationic chaingrowth polymerization, either alone or with other monomers suitable for copolymerization with ethyleneimine, could be used in the present invention. The preferred molecular weight of such a polyethyleneimine could range from about 60,000 to about 1,000,000.

In order to attach the heparin to the amine, the heparin may be subjected to controlled oxidation to provide reactive aldehyde groups on the heparin molecule or the heparin may be attached through its native carboxyl groups by carbodiimide attachment. Oxidation of the heparin molecule is accomplished by treatment of the heparin with periodate or nitrous acid. Preferably, a periodate is added to a buffered aqueous solution of the heparin and allowed to react with the heparin. Any water soluble periodate can be used but preferably the periodate is an alkali metal periodate such as sodium periodate. The amount of periodate required is that sufficient to react with no more than two of the sugar units in the heparin molecule. By sugar, we mean the basic saccharide residues constituting the structure of the glycosaminoglycan. If the periodate used is sodium periodate and the heparin used is a commercially available injectable form of heparin (i.e. its sodium salt with activity of 160 u/mg), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to 8 can be used with lower pH (e.g. an acetate buffer at pH=4.5) being preferred if a rapid reaction is desired while a more neutral pH (e.g. a phosphate buffer at pH=6.88) is preferred for a slower reaction with a longer storage life. With the acetate buffer at a pH of 4.5, the reaction should proceed for about 3 hours while with a phosphate buffer at a pH of 6.88, the reaction should proceed for about 16 hours. If desired, the reacted solution may then be stored prior to use at about 5° C. The storage stability of the reacted mixture at a neutral pH can extend for 2 to 14 days.

When attaching the oxidized heparin, the reaction mixture is first diluted and the pH adjusted in order to bring the pH of the mixture to a pH which is favorable for the coupling reaction. For example, the reaction mixture can be diluted in an acetate buffer solution (pH=4.5). A mild reducing agent such as sodium cyanoborohydride is added to the diluted mixture to effect the reduction of the bonds formed between the reactive aldehyde groups on the oxidized heparin and the aminefunctional groups immobilized on the surface to be treated. The surface to be treated is then immersed in the diluted mixture and incubated at a sufficient temperature and time to complete the reaction. For example, the reaction could be competed in about 1-3 hours at 50° C. At the conclusion of the reaction, the surface is rinsed to remove any loosely bonded heparin.

The surface having immobilized heparin thereon is then provided with an adsorbed protein molecule which is capable of inhibiting the action of a blood coagulation protein to prevent coagulation of fibrinogen. By "protein molecule" we mean any naturally occurring protein or protein fragment which may be activated by heparin to inhibit the coagulation of fibrinogen. A preferred protein is antithrombin III which is known to be activated by heparin to inactivate thrombin. The protein can be adsorbed onto the surface with immobilized heparin immediately before the device is brought into contact with a patient's blood (e.g. by the surgeon immediately before a medical device is implanted) or, the immobilized heparin with adsorbed protein can be provided in a sterile device by drying the device with the immobilized heparin and adsorbed protein thereon and then packaging and sterilizing the device by conventional means. The protein can be easily bound to the heparinized surface by adsorption. For example, antithrombin III can be incubated in contact with a heparinized surface in a HEPES buffer solution for a few minutes followed by rinsing the surface to remove non-bound antithrombin.

The following Examples 1 and 2 show how a heparin coating can be provided on a surface and how antithrombin III can be provided on the heparin coating.

EXAMPLE 1

A piece of coiled tantalum wire was ultrasonically cleaned in 2% Micro-clean for 30 minutes followed by ultrasonic treatment in deionized water for 30 minutes. This last step was repeated after which the coil was rinsed in isopropanol and dried at 50° C. for 20 minutes.

The cleaned coil was swirled in a 2% solution of trichlorovinylsilane (Merck Darmstadt, FRG) in xylene for 60 seconds followed by rinsing for 60 seconds in xylene, 60 seconds in isopropanol, 60 seconds in water and finally in acetone. The coil was then allowed to air dry overnight.

The dried coil was then placed into a glass tube which was filled with 15 ml of an aqueous solution of 35 wt % of freshly distilled acrylic acid and 5 wt % acrylamide. To the 15 ml of monomer solution, 0.9 ml of a solution of ceric ammonium nitrate (0.1M) in nitric acid (0.1M) was added. Deaeration was performed for 3–5 minutes at about 18 mm Hg followed by ultrasonic treatment for 10 minutes and an additional incubation of 35–40 minutes, all at room temperature. The grafted samples were then rinsed 10 times with deionized water at 50° C. followed by an overnight incubation at 50° C. Samples taken showed a deep stain when soaked in toluidine blue solution.

A solution of 0.1 wt % PEI (Polymin SN from Basf with a $M_w$ of 60,000) in 0.1M borate pH=9.0 was prepared to which water soluble carbodiimide (1-(3-dimethylaminopropyl)-3-ethylcarbodiimide, HCl, Aldrich) up to a concentration of 0.05M was added. Immediately after dissolution of the carbodiimide, the grafted coils were contacted with the solution for 50 minutes while gently shaking. After copious rinsing with water, the coil was ready for heparinization.

Oxidized heparin was prepared by adding 0.165 mg $NaIO_4$/ml to 5 mg native heparin (Akzo)/ml 0.05M phosphate buffer (pH=6.88; 0.025M $K_2HPO_4$+$NaH_2PO_4$*$2H_2O$) under the exclusion of light. After overnight oxidation, the resulting heparin solution was diluted in 0.4M acetate pH=4.6 at a ratio of 1:20. 0.1 mg of $NaCNBH_3$/ml was added to the diluted heparin and the coil was incubated in this solution for 2 hours at 50° C. The coil was then rinsed with deionized water, 1M NaCl and water again to remove loosely bonded heparin.

This surface may be provided with antithrombin III by incubation for 15 minutes at 37° C. with HEPES buffer with 500 nM antithrombin. The surface can then be washed to remove unbound antithrombin.

EXAMPLE 2

Polyurethane samples were provided with a grafted polyacrylamide or polyacrylic acid surface. The samples were first corona treated to create reactive groups on the surface. The treated sheets were placed in a 40 weight % solution of acrylamide (or in a solution of 15% acrylic acid and 25% acrylamide) with stirring, to which 1.75 ml. of a ceric ion solution (made by mixing 13.7 grams of ceric ammonium nitrate (CAN) and 15.75 grams of fuming nitric acid with water to an aqueous solution volume of 250 ml.) was added per 100 grams of acrylamide solution. The test samples were then allowed to react with the monomer solution at room temperature for one hour. The test samples were then removed from the monomer solution and thoroughly rinsed with deionized water.

For the samples made with acrylic acid and acrylamide, ethylene diamine was coupled to the carboxyl groups of the grafted polymer by incubating the samples in a buffer solution containing 0.5M ethylene diamine•2HCl and 0.5M 4-morphyleneethanesulfonic acid, brought to pH=5.0. Water soluble carbodiimide was added up to a concentration of 0.1M and amination was conducted for 1 hour at room temperature. Test samples were then thoroughly rinsed in 0.2M acetate buffer pH=4.6, 1M NaCl and copious amounts of water.

The aminated polyurethane samples were provided with covalently attached heparin. The test samples were immersed in a solution of 5 mg heparin (from porcine intestinal mucosa) per ml of buffer solution (0.5M 4-morpholineethanesulfonic acid (MES); pH =5.0). Water soluble carbodiimide (1-(3-dimethylaminopropyl)-3-ethylcarbodiimide hydrochloride (EDC)) was added to a concentration of 0.01M. Oxidized heparin was prepared by adding 0.165 mg $NaIO_4$/ml to 5 mg native heparin (Akzo) /ml 0.05M phosphate buffer (pH=6.88; 0.025M $K_2HPO_4$+ $NaH_2PO_4$*$2H_2O$) under the exclusion of light. After overnight oxidation, the resulting heparin solution was diluted in 0.4M acetate pH=4.6 at a ratio of 1:20. 0.1 mg of $NaCNBH_3$/ ml was added to the diluted heparin and the coil was incubated in this solution for 2 hours at 50° C. The coil was then rinsed with deionized water, 1M NaCl and water again to remove loosely bonded heparin.

Some of the heparinized samples were provided with adsorbed antithrombin III by incubation for 15 minutes at 37° C. with HEPES buffer and 500 nM antithrombin. The remaining heparinized samples were incubated in the same solution without antithrombin.

These test samples were used for comparative testing of the effectiveness of the present invention. A first group of comparative samples included the acrylamide grafted polyurethane with no additional treatment. A second group of comparative samples included the acrylamide grafted polyurethane treated with antithrombin. A third group of comparative samples included the acrylic acid/acrylamide samples with attached heparin but no antithrombin. The examples made according to the invention included the acrylic acid/acrylamide samples with attached heparin and antithrombin.

The test samples were incubated at 37° C. in a platlet-rich plasma (citrated blood collected after venipuncture in the proportion of 1 part 0.12M trisodiumcitrate to 9 parts blood which was then centrifuged for 15 minutes at 250G at room temperature). Coagulation was started by adding $CaCl_2$ (20 mM final concentration) to the plasma. At indicated time points, plasma was transferred into a cuvette with HEPES-EDTA and a thrombin substrate (S2238 from Chromogenics, Sweden). Results were as shown in FIG. 1. The surface with no heparin or antithrombin treatment indicated as curve 1 had an initial spike of thrombin. The surface with antithrombin treatment but no heparin indicated as curve 2 had an initial spike of thrombin that was substantially the same as that for curve 1. The surface with attached heparin but no antithrombin III indicated as curve 3 had no initial thrombin spike but in the 20–30 minute time span had an increase in thrombin production. The surface made according to the invention indicated by curve 4 remained flat throughout the measured time period, thus indicating no thrombin present in the test sample. Observation of the samples was consistent with these results with a clotting time for the heparinized sample of 18.3 minutes without antithrombin and no clotting at all noted during the 60 minute test for the sample with heparin and antithrombin.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. In a method having the steps of: immobilizing heparin by covalent bonding onto a blood contacting surface of a medical device, removing loosely bonded heparin molecules and placing the heparin-immobilized surface of the medical device into contact with a patient's blood, the improvement which comprises:

(a) adsorbing a protein onto the heparin-immobilized surface before placing it into contact with the patient's blood, said protein being capable of being activated by heparin to inhibit the action of a blood coagulation protein to prevent coagulation of fibrinogen; and (b) maintaining the adsorbed protein on the heparin-immobilized surface as it is brought into contact with the patient's blood.

2. The method of claim 1 wherein the protein is antithrombin III.

3. The method of claim 1 or 2 also comprising the step of maintaining the surface in contact with the patient's blood until the blood-contacting surface is passivated by plasma proteins of the patient's blood.

4. In method having the steps of: immobilizing heparin by covalent bonding on a blood contacting surface of a medical device and sterilizing the heparin-immobilized surface of the medical device, the improvement which comprises:

adsorbing a protein onto the heparin-immobilized surface before sterilizing it, said protein being capable of being activated by heparin to inhibit the action of a blood coagulation protein to prevent coagulation of fibrinogen.

5. The method of claim 5 wherein the protein is antithrombin III.

* * * * *